United States Patent [19]
Brandt et al.

[11] Patent Number: 5,306,229
[45] Date of Patent: Apr. 26, 1994

[54] ARTICULAR BANDAGE

[75] Inventors: Dieter Brandt, Düsseldorf; Ingeborg Szlema, Kempen; Hans H. Wetz, Uerikon, all of Fed. Rep. of Germany

[73] Assignee: Beiersdorf Aktiengesellschaft, Hamburg, Fed. Rep. of Germany

[21] Appl. No.: 825,002

[22] Filed: Jan. 24, 1992

[30] Foreign Application Priority Data

Jan. 24, 1991 [DE] Fed. Rep. of Germany ....... 4101965

[51] Int. Cl.$^5$ .......................... A61F 5/00; A61F 13/00
[52] U.S. Cl. ........................................ 602/26; 602/61; 602/64; 602/65
[58] Field of Search ................. 128/112.1; 602/60, 61, 602/62, 63, 64, 26; 2/16, 24, 22, 158, 159, 170

[56] References Cited

U.S. PATENT DOCUMENTS

| | | | |
|---|---|---|---|
| 2,140,598 | 12/1938 | Rhorer | 602/62 |
| 3,406,406 | 10/1968 | Lutz | 602/62 |
| 3,458,867 | 8/1969 | Moore | 602/62 |
| 3,513,842 | 5/1970 | Keenan | 602/63 |
| 3,804,084 | 4/1974 | Lehman | 602/62 |
| 4,150,442 | 4/1979 | Boone | 602/63 |
| 4,287,885 | 9/1981 | Applegate | 602/26 |
| 4,353,362 | 10/1982 | DeMarco | 602/26 |
| 4,445,505 | 5/1984 | Labour | 602/26 |
| 4,476,857 | 10/1984 | Levine | 602/63 |
| 4,700,698 | 10/1987 | Kleylein | 602/26 |
| 4,870,956 | 10/1989 | Fatool | 602/26 |

Primary Examiner—Michael A. Brown
Attorney, Agent, or Firm—Anderson Kill Olick & Oshinsky

[57] ABSTRACT

The articular bandage of elastic bandaging material renders possible a selective transversal friction massage for the speedier rehabilitation of the joint functions of injured joints, such as knee joints, ankle joints, elbow joints, shoulder joints and wrists and, in an applied state, has a pad acting upon the joint which is constructed in the form of a pressure pad (20) which possesses a configuration determined by the bony prominences and tendon attachments of the joint and is constructed in the form of a shaped member from a soft-elastic material, in which at least one friction core of a hard or incompressible material is disposed and is fixed in its position in the material of the shaped member (21 FIG. 1).

9 Claims, 2 Drawing Sheets

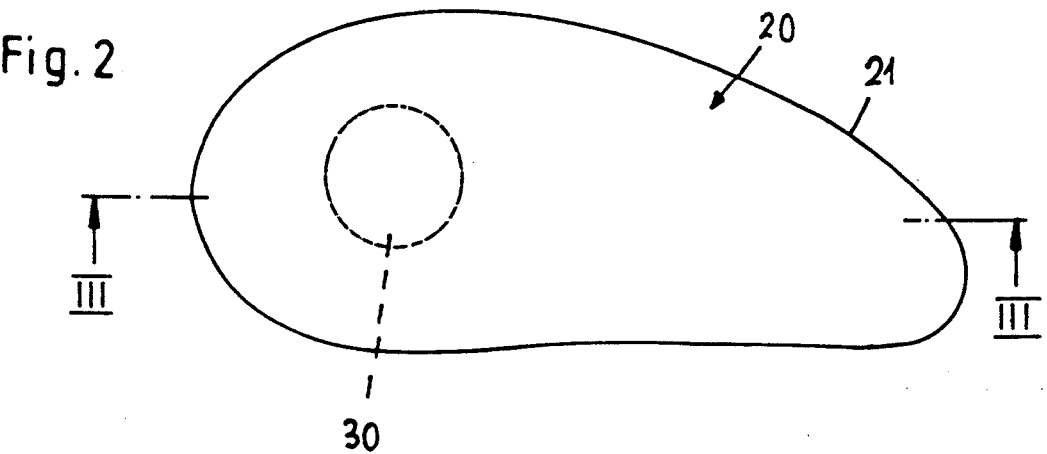
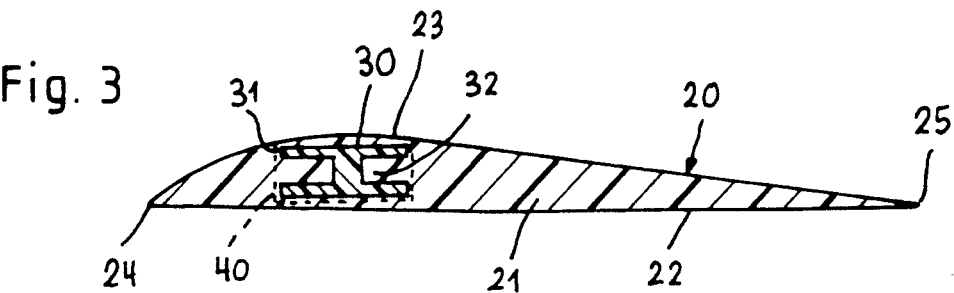
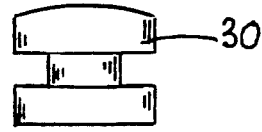
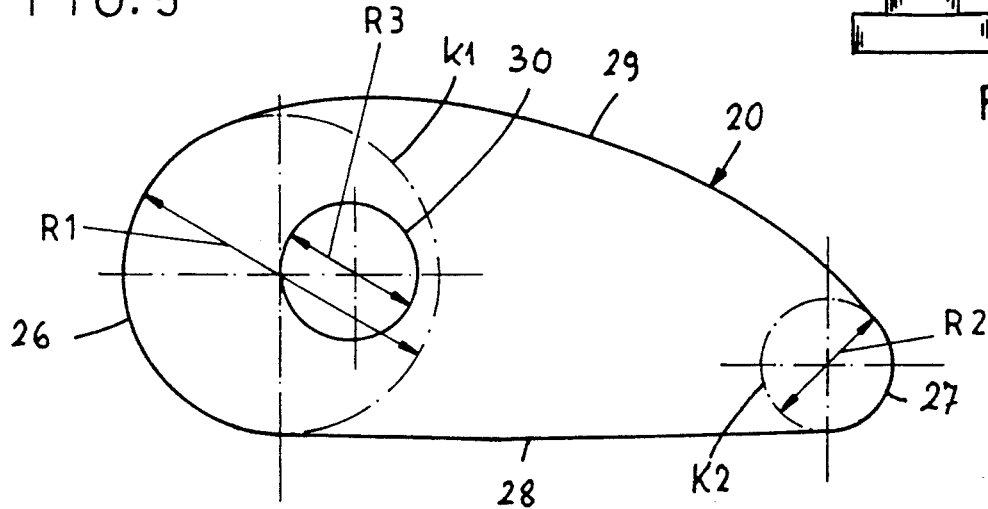
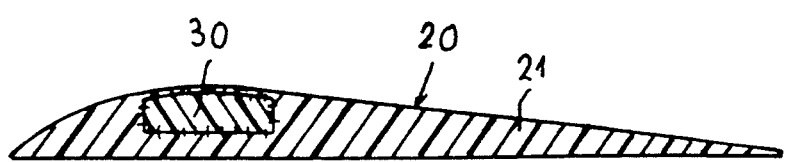

ARTICULAR BANDAGE

FIELD OF THE INVENTION

The present invention relates to an articular bandage of elastic bandaging material, more particularly of tubular or cap-like construction for the speedier rehabilitation of the function of injured joints, such as knee joints, ankle joints, shoulder joints, elbow joints and/or wrists, with at least one pad acting upon the joint in the applied state and constructed in the form of a pressure pad.

BACKGROUND OF THE INVENTION

The bandaging of joints, e.g. subsequent to injuries having been sustained or in the case of degenerative diseases, is a known orthopedic treatment method in which the spectrum ranges from simple wraps with more or less elastic bandages, via ready-to-apply bandages, in the most varied embodiments to expensively constructed splints and braces. The bandages employed in this case are mostly tubular or stocking-shaped and knitted tubularly or flat and, in some embodiments, are laterally reinforced by flattened spiral springs or plastic rods.

From the EP-A-0 027 171, a bandage is known fabricated from elastic bandaging material, particularly in the form of a stocking, for supporting or compressing knee joints, ankle joints, elbow joints and/or wrists, with at least one pressure pad, which, in the applied state, surrounds the bony prominences of the joint and acts upon the adjoining soft joint tissues, in which the pressure pad consists of elastic but incompressible silicone rubber or of a material which possesses the same elasticity and compression properties, on account of the employment of an elastic but incompressible silicone rubber as material for the pressure pad, when the bandage is applied, a massage is obtained which acts solely on the surface of the soft tissues of the joints without any deep action since a silicone rubber which has to possess elastic and incompressible properties, exhibits a low recoil elasticity so that the material displacement necessary for a massage effect, when pressure is applied, does not take place to the extent desired and a massage producing a deep action cannot be achieved. To this is added the circumstance that, for a good circulation in the soft tissues of the joint, it is necessary to produce an adequate alternate load, on account of which the blood is urged out of the soft tissues of the joint located under the pressure pad and flows back again when relieved. However, such an alternate load cannot be achieved with an elastic, incompressible silicone rubber since it proves impossible to produce local pressure forces exerted upon the supporting surface allocated to the pressure component. This is due to the circumstance that the silicone rubber used in this bandage in the form of a pressure pad is not compressed by the application of pressure, but that merely a mass displacement takes place having the effect that the mass components displaced from the pressure-subjected areas emigrate laterally into adjacent areas which are not subject to compression so that, within these adjacent areas, an increase in mass takes place which, in connection with the applied bandage, exercises a massage effect on the pertinent parts of the tissue. However, an alternate load mentioned in the foregoing is not produced; what is being obtained, though, is a good surface massage, but no massage producing a deep action and, consequently, no improvement in the circulation either.

An epicondylitis bandage is known from the EP-A-0-250 409. Such an epicondylitis bandage consists substantially of a tubular section of elastic material, the tensile stress in the circumferential direction being variable by means of a tightening strap with a fastener proceeding essentially in the circumferential direction, while the tubular section mentioned extends substantially uniformly on both sides around the elbow joint. The elastic material of the tubular section is a knitted fabric having a heat-insulating effect. At the points corresponding to the epicondyles, substantially plate-shaped, hard elastic pads are to be found, while the tightening strap between said pads is disposed in such a way that it overlaps the latter at least in part. With an epicondylitis bandage constructed in this manner, the compression effect is produced by a strap engaging around the arm with the aid of small plates which are allocated to the positions of the epicondyles. In this case, the strap and the small plates are rigidly connected to an elastic arm bandage. In this case the arm bandage encloses a portion of the forearm, the elbow and a portion of the upper arm and is very highly slip-proof and is intended to ensure the medically correct position of the tightening strap with small plates even when the tightening strap is tightened only slightly. An additional thermal effect of the bandage is intended to be achieved particularly in those cases where a heat-insulating textile or other layer is additionally provided, it being possible, however, to incorporate an additional thermally insulating thread material into the fabric or knit.

The DE-U-84 10 987.4 further describes a bandage for the treatment of epicondylitis which serves to treat epicondylitis by exerting a pressure on the extensor musculature of the forearm, it comprises a strap for relieving the muscles which touch the epicondyles with a fastener disposed at its ends for forming an adjustable annular element, the strap is fitted with at least one pressure plate or with two pressure plates disposed so as to be spaced apart from each other, the pressure plates, for the purpose of alignment or for an opposing arrangement of the pressure plates on the forearm, are disposed on the strap in such a way as to be displaceable and adjustable. It is supposed to be possible with a thusly constructed bandage, while taking the wearing comfort into consideration, to construct an efficient, individually adaptable arrangement that renders possible the adjustment of the pressure plates into the required position.

Compression pads and pressure plates are employed in these known bandages which, facing the side of the joint, do not possess any specially constructed surface structures but which are constructed so as to be flat while, in the first case of the compression pad, a pressure is exerted on the soft joint tissues for producing a mechanical stimulus to bring about speedy decongestion of the ecchymoses of articular injuries by achieving a rolling effect that brings about an intensive massage of the soft tissues of the joint due to the elastic but incompressible silicone rubber used. Whereas the pressure plates used merely bring about an increased pressure on the tendon fibers at their attachment points, viz. the epicondyles. However, in both cases no specific frictional massage is carried out on particular painful points, i.e. no form of massage is provided in which the tendon attachments are treated transversely to the attachment. The combination of a massage of the soft tissues of the joint cannot be achieved with any of the known bandages.

It is therefore the object of the invention to provide an articular bandage which, with the aid of a selective, strictly locally applied transversal friction massage, gently supports an active exercise treatment. Another object of the invention is to provide a bandage which renders possible a speedier rehabilitation of the joint functions of injured joints, as well as, over and above the effect of alleviating the pain, exercising a healing effect.

SUMMARY OF THE INVENTION

This and other objects of the invention, which shall become hereafter apparent, are achieved by the disclosed articular bandage constructed according to the invention. The bandage supports the exercise treatment in a gentle manner and thereby renders possible a speedier rehabilitation of the joint functions. Apart from the pain alleviation effect, a remedial effect is achieved as well. The effect obtained with the bandage is based on the factors relief, compression, and friction massage, while the bandage itself guides, pads, and, to a limited extent, stabilizes the joint. A compressive pressure on the soft tissues of the joint and on the tendon attachments is produced and, when moving, an intermittent massage on the participating muscles is effected. Due to the hard friction core disposed in the pressure pad, besides a massage of the soft tissue of the joint, a selective friction massage on special painful points is possible with the aid of the pad material. In this form of massage the tendon attachments are treated transversely to the attachments, the transverse friction being applied strictly locally. In acute cases, this friction massage counteracts a formation of adhesions with adjoining structures and, in subacute or chronic cases, detaches existing adhesions.

At the same time, due to the release of histamine and erotonin from the destroyed mastocytes, the friction massage eliminates local inflammation reactions biochemically and thus results in an analgesia. The ideal orthometric configuration differs for each joint and is adapted to the anatomic shape of the joint in question, in which connection the bandages for knee joints, ankle joints, elbow joints and/or wrists possess an identical preferably basic construction:

Three-dimensioned anatomical shape knitting in the functional flexion position of the joint;—compressive pressure 15 mm Hg;—two-way stretch elastic and, thereby, balanced pressure distribution in both directions; specially constructed termination of the bandage edges with pressure-reducing margin, so that no congestive pain appears insofar as tubular bandages are involved; viscoelastic contour pads of silicone in the form of active elements; bony prominences and tendon attachments determine the shape of the pad; two-component pad with a fixed, hard friction core for the selective friction massage of the critical points (tendon attachments); pads of highly elastic, relief knitted fabric within whose area the material is gathered according to the bellows principle in a wave-like manner. In this case the waves permit a high degree of mobility, absorb the surplus material during the flexion of the joint and prevent creases from forming; skin-compatible fabrics of, e.g., cross-linked polyurethane (trade name ELASTHAN), elastodiene fibers and polyamide having a high proportion of cotton; it being also possible to employ elastofibers which, on account of their chemical structure, are deformable to an exceedingly high degree and possess the property of substantially at once, and almost completely, returning to the original state after the neutralization of the forces of deformation, i.e. they are such highly elastic fibers which possess a high degree of elastic elongation. These highly elastic fibers may consist of rubber threads, of rubber, and of other synthetic elastomeric fibers which are not produced on a polyurethane basis. In the case of the elastadiene fibers, fibers of natural polyisoprene (rubber), or of synthetic polyisoprene or of such polymers which result from the polymerization of one or more dienes, possibly with the addition of one or several vinyl monomers are involved.

Advantageous embodiments of the invention are characterized in the subclaims.

BRIEF DESCRIPTION OF THE DRAWINGS

FIG. 2 depicts the pressure pad in a top view;

FIG. 3 depicts a vertical, longitudinal, cross-sectional view in the direction of Line III—III in FIG. 2;

FIG. 4 depicts a friction core in an enlarged side elevational view;

FIG. 5 depicts, in a top view, the pressure pad with base circles shown in the curved narrow side areas of the pad shaped member; and FIG. 6 depicts, in a vertical, longitudinal cross-sectional view, a further embodiment of a pressure pad with a friction core incorporated into the material of the latter.

DETAILED DESCRIPTION OF THE PREFERRED EMBODIMENT AND ALTERNATE EMBODIMENTS

Figure 1:
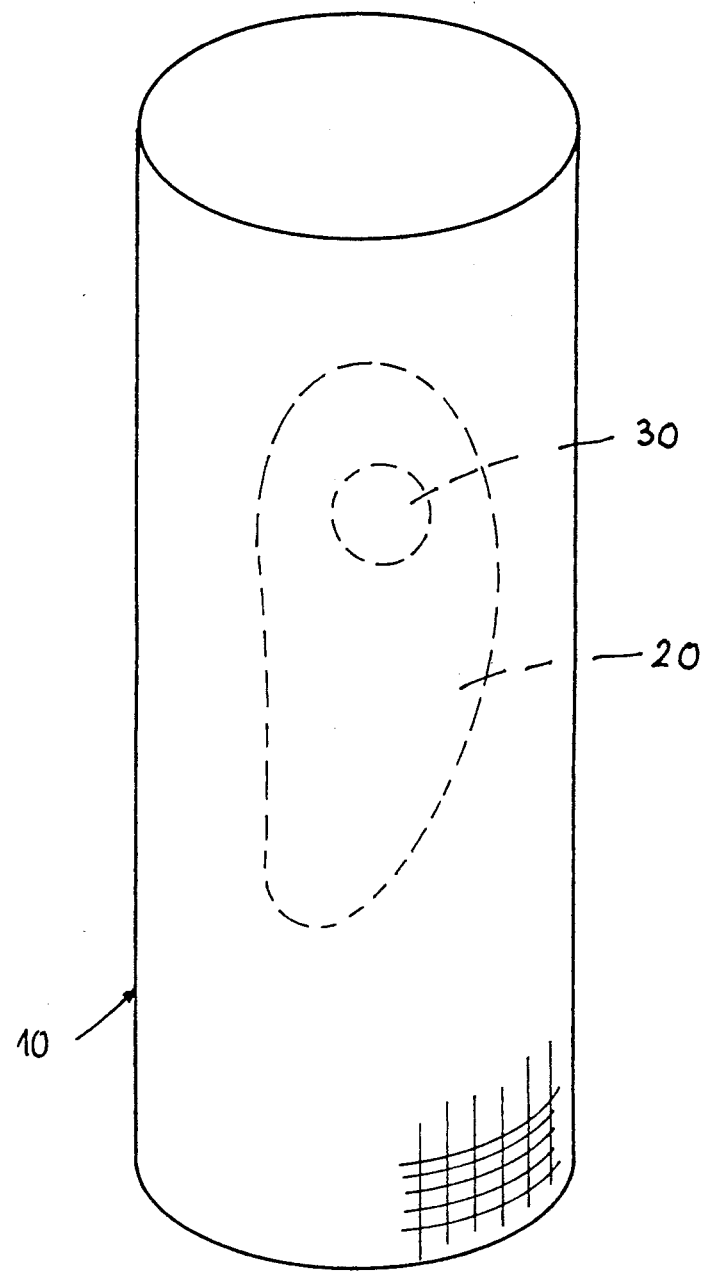
FIG. 1 depicts, in a perspective view, an articular bandage with a top view of a pressure pad disposed on the same.

Referring now to the drawings wherein like numerals reflect like elements throughout the several views, the pressure pad depicted in FIGS. 2 and 3 and identified with 20 is made use of as a pad in a bandage 10 constructed preferably in a tubular or cap-shaped form from an elastic bandaging material, e.g. an elastic fabric, a finely or coarsely knitted fabric (FIG. 1). Such an articular bandage 10 can be fitted on to a knee joint, ankle joint, shoulder joint, elbow joint and/or wrists, while, in the applied state, the pressure pad 20 acts upon the joint in such a way that a compressive pressure is exerted on the soft tissues of the joint and the tendon attachments, and a selective friction massage is performed on special painful points. In order to attach the pressure pad 20 to the bandage 10, the latter is preferably constructed with two layers within the attachment area; the pressure pad 20 being then disposed within the interspace formed by this double layer construction, the pad having the configuration shown in the FIGS. 2 and 3. However, other known forms of attachment are also possible for the pressure pad; for instance, welded, bonded or sewn connections.

The pressure pad 20 is constructed having the form of a shaped member 21 and possesses a configuration that is predetermined by the bony prominences and tendon attachments. The shaped member 21 of the pressure pad 20 consists of a soft elastic material.

Fixed in the material of the shaped member 21 is a solid friction core 30 which consists of a hard material, such as, e.g., an incompressible polyamide, polyurethane, silicone rubber or of a material which possesses the same elasticity properties or of an inelastic material.

This friction core 30 is constructed in a disk-shaped or beam-shaped manner or possesses a cross-section having some other geometric form and, within the area of its circumferential wall area 31, has a constricted portion in the form of a groove 32, groovelike recesses, undercuts, serrations, or the like, which serves to accommodate the material of the shaped member so that the friction core 30 is fixed in its position in the shaped member 21 of the pressure pad 20. By way of preference, the disposition of the friction core 30 is chosen in such a way that the same comes to lie closely underneath the surface of the shaped member 21 so as to be able to exert a strong pressure on the joint (FIG. 4).

The shaped member 21 consists of a soft or soft-elastic material. In contrast thereto the friction core 30 consists of a hard or incompressible material; it is fixed in its position in the material of the shaped member 21. In comparison with the hardness of the shaped member 21, the friction core 30 is of a greater hardness. The difference between the hardness of the shaped member 21 and the hardness of the friction core 30 is at least 10 Shore A, preferably though 20 Short A.

The hardness of the material of which the shaped member 21 consists is below 50 Shore A, whereas the hardness of the material from which the friction core 30 is fabricated, is above 50 Shore A, this will be dealt with in greater detail hereinafter.

The pressure pad 20 preferably possesses the shape shown in FIGS. 2 and 3. According to these, the shaped member 21 is provided with a flat base 22 and an outer convexity which faces away from the base and which tapers conically from one end 24 to the other end 25 of the shaped member 21. The friction core 30 is preferably disposed in the shaped member 21 within that area of the outer convexity which has the largest cross-section (FIG. 3).

The shaped member 21 itself possesses an approximately rectangular shape having longitudinal sides 28,29 tapering conically in the direction towards the end 25 of the shaped member 21, whose longitudinal side proceeds curvedly and the longitudinal side 28 proceeds almost linearly, preferably with a slight constriction and with curvedly constructed sides 26,27, while the two curved narrow sides are based on different circle diameters R1, R2. The circle diameter R1 of the circle K1, upon which the curved narrow side 26 is based, is, in the embodiment shown in FIG. 5, approximately 4 cm, and the circle diameter R2 of the circle K2, upon which the curved narrow side 27 is based, approximately 2 cm, while the shaped member 21 has a length of approximately 11 cm and a height of the outer convexity of approximately 1 cm, within the area of the narrow side 26. A pressure pad 20 possessing these dimensions may, for example, be used in an elbow bandage. However, departures from these dimensions are possible.

The shaped member 21 consists of a soft or a soft-elastic material, such as felt, cellular rubber, neoprene, rubber, viscoelastic silicone rubber, or of an elastic, pressure-deformable silicone rubber having, e.g., a hardness of 40 Shore A; a silicone foam having a hardness of from 9 to 13 Shore A or a compressible, pressure-deformable silicone rubber which reassumes its shape without the resilience of the type of a cold rubber which is vulcanized according to the polyaddition process, which, apart from a high degree of flexibility, possesses a hardness which is below 4 Shore A, it being also possible in this case, for silicone rubber to be employed whose hardness lies above 4 Shore A. Such viscoelastic silicone rubbers or materials which possess the same elasticity qualities, possess the characteristic that, when the bandage with such a pressure pad is applied on account of the gliding motion set off by mass displacement, it acts as a massage within the contact area when pressure is applied during motion sequences. For the manufacture of the shaped member 21, a material should be selected which is viscoelastic and, due to its elastic qualities, performs a massage.

In contrast hereto the friction core 30 of the pressure pad 20 consists of a hard or incompressible plastic having, e.g., hardness in excess of 50 Shore A and, vis-a-vis the shaped ember 21, possesses a greatly superior hardness so that, when moving, a selective friction massage is achieved on special painful points. As material for the friction core, natural or synthetic rubber or hard rubber is used. Thus, a chloroprene polymerisate (trade name NEOPREN) having a hardness of 50 Shore A, a rubber-elastic, cross-linked polyurethane (trade name VULKOLLAN) having a hardness of from 65 to 90 Shore A; a silicone rubber having a hardness of 60 Shore A; an ethylene-propylene-diene rubber (EPDM) having a hardness of 80 Shore A; or a copolymerisate with acrylonitrile (trade name PERBUNAN) having a hardness of 70 Shore A, further a polyamide may be employed. It is possible, however, to also use other plastics or natural material derivations for producing the core 30. What is essential, though, is that the core 30 has an adequate hardness in order to be capable of performing the selective frictional massage on special painful points. The friction core 30 may also consist of metal or wood.

The disposition of the pressure pad 20 in the bandage is such that the outer convexity 23 of the pressure pad 20 faces towards the joint. Depending on the type of joint, it is also possible for more than one pressure pad to be disposed in the bandage 10. Moreover, the pressure pad can be provided with several individual friction cores 30 in order to act on several painful points simultaneously.

The friction core 30 which has a button-like shape, or any other geometric form, is firmly inserted into the pressure pad 20 and terminates in a spherical manner on the surface of the pressure pad. In order to secure the position, i.e. for securing against a displacement or traveling of the core 30 in the pressure pad 20, the core is provided with a surface contouring with undercuts or serrations, into which the material of the pad engages. It is essential that the friction core 30 consists of a material which is somewhat harder than the material of the pressure pad. Thus the possibility also exists of employing for the pressure pad having a hardness of 4 Shore A and for the friction core 30 a material whose hardness is e.g. 15 Shore A. When the bandage is applied, the friction core 30 rests on the tendon attachment, whereas the pressure pad 20 itself rests upon the muscle and/or on the soft tissues of the joint. The pressure pad may also be disposed on both sides of the bandage. According to a further embodiment of the invention, the friction core 30 in the pressure pad 20 is disposed in such a way as to be replaceable. For this purpose, the shaped member 21 is provided with a recess 40 having approximately the size of the friction core 30, into which the friction core 30 is pressed by means of a light pressure (FIG. 3).

The inner wall area which delimits the recess in the pressure pad 20 possesses a contour configuration which renders possible an engagement into the contour of the circumferential wall area of the friction core 30.

Since the pad material is elastic, the friction core 30, however, possesses a greater hardness when compared with the material of the pressure pad. The friction core 30 allows itself to be pressed into the recess while during the pressing operation, the contour of the inner wall area is compressed in such a way that the core 30 is capable of sliding completely into the recess 40. Due to the elastic recovery capability of the pressure pad 20 material, the pressure pad material is urged into the marginal contour of the friction core 30 so that the latter is retained rigidly in the pressure pad. By means of an appropriate deformation of the pressure pad through a powerful external application of pressure, the core 30 can be pressed out from the pressure pad. The possibility is provided, thereby, of being able to use friction cores that possess different hardnesses. In the case where the pressure pads 20 are used with interchangeable friction cores 30, the pressure pad is attached to the bandage in such a way that a detachment of the pressure pad is possible.

The friction core 30 can be constructed in the form of a shaped member; in that case it is disposed within the material of the shaped member 21. According to a further embodiment of the invention, the material of the friction core 30, consisting of a plastic, (e.g. silicone rubber), is fused with the material of the shaped member 21 and is undetachably connected to the shaped member 21 (FIG. 6). The friction core 30 may also be obtained in the course of the manufacturing process of the shaped member 21 by means of the material hardening or curing of a section which is intended to form the future friction core and which consequently possesses a greater hardness when compared with the soft material of the shaped member 21. In both cases, silicone rubber should preferably be used as material.

Furthermore, the shaped member 21 may also be constructed in such a way as to have a pouch-like configuration. Said pouch consists of soft elastic plastics. The interior of the pouch is filled with a gaseous medium, such as air, or with a liquid medium, such as a viscous silicone oil, water or the like. The friction core 30 is in this case fixed in its position on the inner wall area of the pouch. Apart from the construction of the pressure pod 20 with one or with several friction cores 30, the bandage itself may also be provided on two sides facing each other with pressure pads 20 fitted with friction cores 30.

While the preferred and alternate embodiments of the invention have been depicted in detail, various modifications and adaptations may be made thereto, without departing from the spirit and scope of the invention as delineated in the following claims.

We claim:

1. An articular bandage of elastic bandage material, more particularly of tubular or cap-like construction for the speedier rehabilitation of the function of injured joints such as knee joints, ankle joint, shoulder joints, elbow joints and/or wrist joints, comprising:

at least one pressure pad comprising a shaped member acting upon the joint in the applied state and possessing a configuration determined by the bony prominences and tendon attachments of the joint and fabricated from a soft elastic material shaped member, wherein said shaped member possesses a hardness below 50 Shore A; and at least one friction core of a hard or incompressible material, having a hardness above 50 Shore A, disposed and fixed in its position in the material of the shaped member, wherein the friction core has a hardness exceeding the hardness of the material of the shaped member, constructed in a disk-shaped form and having a circular diameter and groove-like recesses in order to secure its position in the shaped member of the pressure pad, within its circumferential wall area or accommodating the material of the shaped member, wherein the difference between the hardness of the shaped member and the hardness of the friction core is between 10 and 20 Shore A.

2. An articular bandage of elastic bandage material, more particularly of tubular or cap-like construction for the speedies rehabilitation of the function of injured joints, such as knee joints, ankle joints, shoulder joints, elbow joints and/or wrist joints, comprising:

at least one pressure pad comprising a shaped member, having a flat base and an outer convexity facing away from the base, said shaped member acting upon the joint in the applied state and possessing a configuration determined by the bony prominences and tendon attachments of the joint and fabricated from a soft, elastic material, wherein said shaped member possesses a hardness below 50 Shore A, wherein the outer convexity of the shaped member tapers conically from one end to the other end and in that the friction care is disposed within an area of the outer convexity which possesses the largest diameter, wherein the shaped member has an approximately rectangular configuration with longitudinal sides tapering conically into a shaped member end and has curvedly constructed narrow sides and the curved narrow sides are based on different circular diameters;

at least one friction core of a hard or incompressible material, having a hardness above 50 Shore A, disposed and fixed in its position in the material of the shaped member, wherein the friction core has a hardness exceeding the hardness of the hardness of the shaped member and the hardness of the friction core is between 10 and 20 Shore A wherein the friction core is obtained during the manufacture of the shaped member by material curing or hardening of a section of the shaped member and the friction core and the shaped member is comprised of plastics, more particularly or silicone rubbers possessing different degrees of hardness; and wherein the diameter of a circle upon which one of the curved narrow side is based is approximately 4 cm, and the diameter of a circle forming the basis of the other curved narrow side is approximately 2 cm and has a length of the shaped member of approximately 11 cm and a height of the outer convexity of approximately 1 cm within the area of the narrow side.

3. The articular bandage of claim 2, wherein the shaped member (21) consists of felt, cellular rubber, neoprene, rubber, a viscoelastic silicon rubber or an elastic, compressible, pressure-deformable silicone rubber or of a material which possesses the same elasticity qualities as natural rubber or silicone rubber.

4. The articular bandage of claim 3, wherein the shaped member is constructed in the form of pouch and is provided with a filling of gaseous or liquid medium, while the friction core is fixed in its position on the inner wall of the pouch.

5. The articular bandage of claim 4, wherein the friction core is comprised of an incompressible plastic, such as natural or synthetic rubber, hard rubber, chloroprenepolymerisate, rubber-elastic cross-linked polyurethane, polyamide, metal or wood.

6. The articular bandage of claim 5, wherein the bandage has two oppositely located sides with pressure pads filled with friction cores.

7. The articular bandage of claim 6, wherein a recess is constructed in the shaped member of the pressure pad for accommodating the friction core.

8. The articular bandage of claim 7, wherein the friction core is detachably retained in the recess by a press or force fit.

9. The articular bandage of claim 8, wherein an upper wall area of the friction core is constructed to be curved, semicircular or flat with rounded-off corners.

* * * * *